United States Patent [19]
Drabb, Jr. et al.

[11] 4,191,768
[45] Mar. 4, 1980

[54] PENTADIENONE HYDRAZONES, METHOD FOR PREPARING THE SAME, AND INSECTICIDAL USE THEREOF

[75] Inventors: Thomas W. Drabb, Jr., Trenton; James B. Lovell, Pennington, both of N.J.

[73] Assignee: American Cyanamid Company, Stamford, Conn.

[21] Appl. No.: 934,441

[22] Filed: Aug. 17, 1978

[51] Int. Cl.² ............... A01N 9/20; C07D 233/52
[52] U.S. Cl. .................... 424/251; 260/566 B; 260/564 F; 424/244; 424/273 R; 424/327; 542/417
[58] Field of Search ............... 260/566 B, 564 F; 424/327, 251; 542/417

[56] References Cited

U.S. PATENT DOCUMENTS

| | | | |
|---|---|---|---|
| 3,636,112 | 1/1972 | Draber et al. | 424/327 X |
| 3,732,307 | 5/1973 | Middleton | 424/327 X |
| 3,867,449 | 2/1975 | Moore | 424/327 X |
| 4,087,525 | 5/1978 | Lovell | 424/327 X |

*Primary Examiner*—Arthur P. Demers
*Attorney, Agent, or Firm*—Harry H. Kline

[57] ABSTRACT

There are provided insecticidal pentadienone hydrazones and methods of preparation thereof. There is further provided a method for using the aforesaid compounds for the control of insects, especially Lepidopterous insects, and for the control of ants, Family Formicidae, especially fire ants.

9 Claims, No Drawings

PENTADIENONE HYDRAZONES, METHOD FOR PREPARING THE SAME, AND INSECTICIDAL USE THEREOF

The present invention relates to novel insecticidal pentadienone hydrazones. More particularly, it relates to pentadienone hydrazones of the structure represented by formula:

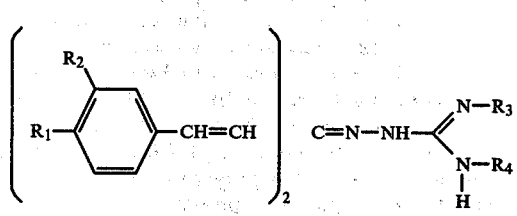

wherein $R_1$ and $R_2$ are each selected from $Y-CF_2X-$, hydrogen or halo, provided that at least one but not both of $R_1$ and $R_2$ is $Y-CF_2X-$; Y is selected from hydrogen, fluorine, $-CHF_2$ or $-CHCl_2$; X is oxygen or sulfur; $R_3$ and $R_4$ each are alkyl ($C_1$-$C_4$) and, when taken together they form an alkylene group of 2 to 4 carbon atoms or a methyl or a dimethyl-substituted alkylene group of 2 to 4 carbon atoms, and the inorganic acid addition salts thereof.

A preferred group of compounds represented by hereinabove defined structure are those wherein $R_1$ is selected from $CHF_2O-$, $CHF_2S-$, $CF_3O-$, $CF_3S-$ or $CHF_2-CF_2O-$; $R_2$ is hydrogen; and $R_3$ and $R_4$ taken together with the amidino group

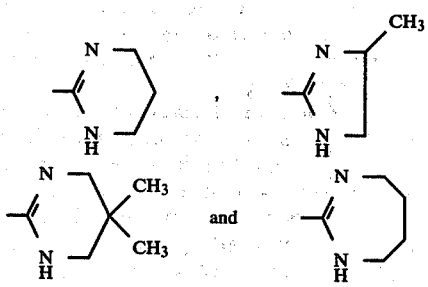

they are attached to represent the moieties

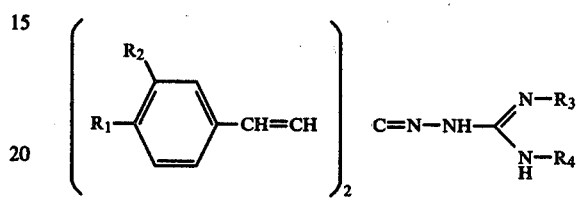

and the acid addition salts thereof, preferably the hydrochloride, hydrobromide or hydriodide.

Among the compounds of the invention which can be prepared in accordance with the invention are illustratively: 1,5-bis[p-(trifluoromethylthio)phenyl]-1,4-pentadien-3-one (4-methyl-2-imidazolin-2-yl)hydrazone; 1,5-bis[p-(trifluoromethylthio)phenyl]-1,4-pentadien-3-one (1,4,5,6-tetrahydro-5,5-dimethyl-2-pyrimidinyl)hydrazone; 1,5-bis[p-(trifluoromethoxy)phenyl]-1,4-pentadien-3-one (4,5,6,7-tetrahydro-1H-1,3-diazepin-2-yl)hydrazone; 1,5-bis[m-(difluoromethoxy)phenyl]-1,4-pentadien-3-one (1,4,5,6-tetrahydro-2-pyrimidinyl)hydrazone; 1,5-bis[p-(1,1,2,2-tetrafluoroethoxy)phenyl]-1,4-pentadien-3-one (1,4,5,6-tetrahydro-5,5-dimethyl-2-pyrimidinyl)hydrazone; 1,5-bis{p-[(difluoromethyl)thio]phenyl}-1,4-pentadien-3-one (1,4,5,6-tetrahydro-5,5-dimethyl-2-pyrimidinyl)hydrazone; and 1,5-bis[p-(difluoromethoxy)phenyl]-1,4-pentadien-3-one (1,4,5,6-tetrahydro-5,5-dimethyl-2-pyrimidinyl)hydrazone; and acid addition salts thereof, preferably the hydrochloride, hydrobromide or hydriodide.

Advantageously, the compounds of the invention find utility in controlling insects, particularly Lepidopterous insects, and ants, Family Formicidae, by contacting the insects with, and/or applying to their habitat or food supply, an insecticidally effective amount of a pentadienone hydrazone of the structure:

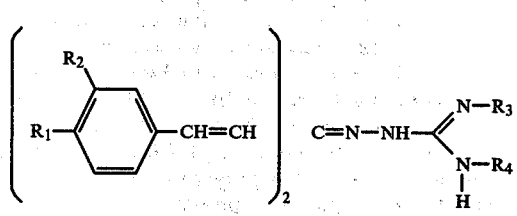

wherein $R_1$, $R_2$, $R_3$ and $R_4$ are as hereinabove defined; and salts thereof. Further, the invention finds utility in protecting agronomic crops, trees, shrubs, ornamentals, and the like from attack by insects, by applying to the crops an insecticidally effective amount of a compound having the above-identified structure.

It is unexpectedly found that the insecticidal pentadienone hydrazones of the present invention can be conveniently prepared by a reaction sequence graphically illustrated and described as follows:

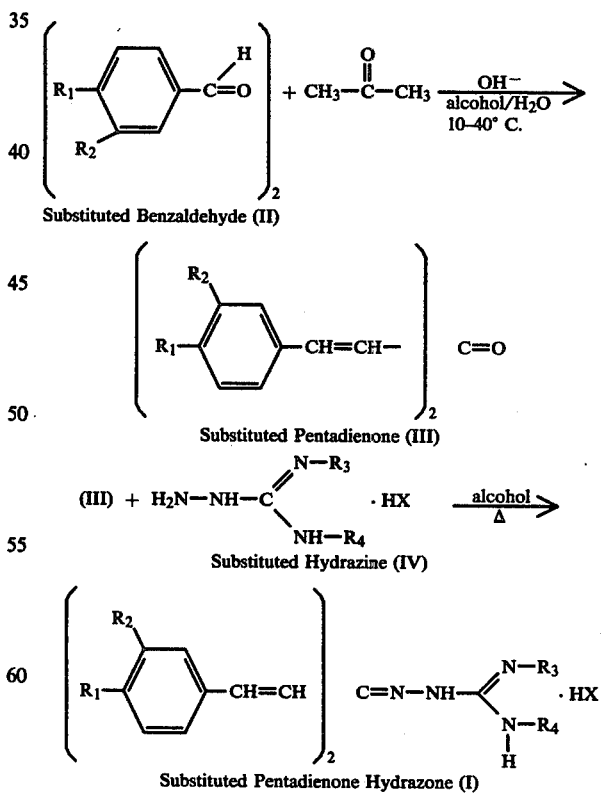

wherein each of the R groups are as hereinabove defined and HX represents a mono or divalent inorganic acid, such as hydrochloric, hydrobromic or hydriodic acid. In the above sequence, the desired product (1) is shown as the HX salt. The corresponding pentadienone hydrazone free base may be obtained by treating the HX salt with an aqueous solution of a base, such as sodium or potassium bicarbonate, sodium or potassium carbonate, sodium or potassium hydroxide or ammonium hydroxide.

As above illustrated, two moles of a substituted benzaldehyde (II) are reacted with one mole of acetone in an aqueous alcohol in the presence of an alkali metal base such as sodium or potassium hydroxide at a temperature range of 10° to 40° C., preferably 20° to 25° C. for a period of time from one to three hours, or until the condensation reaction is essentially complete to yield the corresponding pentadienone (III). Next, the so-obtained pentadienone is condensed with an equimolar (or, if desired, slight excess) amount of a salt of the appropriate hydrazine (IV) in an alcohol at 50° C. to 80° C. or at the boiling point of said alcohol for a period of time of one to five hours or until the condensation reaction is essentially complete to yield the salt of a pentadienone hydrazone (I). Exemplary of the alcohols used in the above reaction sequences are methanol, ethanol, isopropanol, and mixtures thereof. The pentadienone hydrazone may be recovered from the above salt, if desired, by treating said salt with a dilute aqueous solution of an inorganic base, such as sodium or potassium bicarbonate, sodium or potassium carbonate, sodium or potassium hydroxide, or ammonium hydroxide.

In accordance with this invention, it is found that both control of insects, particularly Lepidopterous insects, and protection of agronomic crops, trees, shrubs and ornamentals from attack by the insects, can be achieved by the application of an insecticidally effective amount of a pentadienone hydrazone to the crops or to the habitat of the insects. In practice, from about 0.14 kg/hectare to 11.2 kg/hectare, and preferably 0.56 kg/hectare to 4.48 kg/hectare of the pentadienone hydrazone is effective for insect control and/or for crop protection.

The desired pentadienone hydrazones can be applied in either liquid or solid form. For instance, they may be applied in solid form as dusts or dust concentrates, or in liquid form as emulsifiable concentrates, flowable liquids or wettable powders which are dispersed in water or other inexpensive liquid for application as a finely divided spray.

A typical emulsifiable concentrate can be prepared by admixing from about 12% to 29% by weight of a pentadienone hydrazone, about 8% to 12% by weight of a blend of nonionic emulsifiers, such as T-Mulz 339 (sold by Thompson-Hayward of Kansas City, Kansas), or polyoxyethylene derivatives and blends with alkyl aryl sulfonates, and about 59% to 80% by weight of cyclohexanone or a heavy aromatic solvent having a mixed aniline point between −1° C. and 35.0° C. (30° F. and 95° F.), a specific gravity between 0.880 and 1.5 at 15.5°/15.5° C. (60°/60° F.), and an aromatic content of 60% to 100%. These formulations provide from 119.8 g/liter to 239.6 g/liter of the active hydrazone, and are generally diluted with water for application as a dilute liquid. However, said formulations can also be applied in the form of undiluted discrete droplets as low volume or ultra-low volume sprays. For such application, the emulsifiable concentrate is usually applied with apparatus designed to disperse the liquid in the form of finely divided discrete droplets having a mass median diameter of from 25 to 150 microns.

A typical wettable powder formulation can be prepared by grinding together about 34% by weight of a synthetic calcium silicate, 12% by weight of a dispersing agent such as sodium lignosulfonate, 4% by weight of a wetting agent such as an alkyl aryl sulfonate, and 50% by weight of the pentadienone hydrazone. Such formulation is generally dispersed in water for application as a liquid spray.

In general, the pentadienone hydrazones of this invention are especially active and quite selective against Lepidopterous larvae such as southern armyworms [*Spodoptera eridania* (Cramer)], cabbage loopers [*Trichoplusia ni* (Hübner)], tobacco budworms [*Heliothis virescens* (Fabricius)], and the like, at 10 to 1000 ppm rates. They do not appear to be especially toxic to most beneficial insects and thus are useful for pest management and integrated control programs. Moreover, these compounds show virtually no phytotoxicity to plants at rates of application up to 11.2 kg/hectare.

Advantageously, the pentadien-3-one hydrazone compounds of the present invention are active as stomach poisons. Thus, they are effective against insects with chewing mouth parts (Orthopterous insects such as cockroaches, grasshoppers, crickets and Isopterous insects, such as termites) as well as those with sponge and lapping mouth parts (Dipterous insects, such as flies). They are effective for the control of fire ants, such as the southern fire ant, *Solenopsis xyloni*, the black imported fire ant, *Solenopsis richteri* and the red imported fire ant, *Solenopsis invicta*. They are also effective for the control of ants, such as the big-headed ant, *Pheidole megacephala*, and the Argentine ant, *Iridomyrmax humilis*, that are dominant pests in pineapple and sugarcane fields, and for the control of many species of ants that are classified under the general category of household ants. Ants are serious economic and public health pests. Serious problems created by fire ants are stinging of humans and livestock, feeding on plants, particularly on seedlings and on germinating seeds, damage to farm machinery that strike ant mounds, loss of crops and refusal of workers to enter infested fields to cultivate and harvest crops. Ants invade houses, crawl over food, carry bits of food to their nests and also cause damage by establishing their nests in the woodwork of houses and other wooden buildings.

Control of these pests can be achieved with treated baits that are distributed in or adjacent to the infested area, such as pasture, park dwellings or other locations in which ant control is desired, and made available to worker ants. The workers carry the treated bait to the colony where it is consumed by the queens and the young ants, leading to their destruction.

In practice, generally about 1.25 g/ha to 75.0 g/ha, and preferably 2.5 g/ha to 37.5 g/ha of the pentadienone hydrazone is effective for fire ant control and/or for crop protection from ants and about 0.0625% to 4% by weight, and preferably 0.125% to 2.0% by weight of the pentadienone hydrazone is effective for the control of house ants and/or other insects that are controlled by bait.

Baits can be prepared, for example, by admixing the pentadienone hydrazone with peanut butter or citrus pulp, vegetable oils such as soybean oil, animal fats such as lard and tallow, and with or without an organic filler such as bran, and/or an attractant such as lecithin. The composition is then placed in soda straws or on a carrier such as puffed grain, corncob grits and/or starch matrix and distributed in the area of the colony or infestation.

Use of these baits has particular advantage, since such method of distribution poses little or no hazard to non-target organisms that may frequent the infested area.

The invention is further illustrated by the examples set forth below. These examples are provided only by way of illustration and are not intended to be limiting. All parts, unless otherwise noted, are by weight.

EXAMPLE 1

Preparation of p-Trifluoromethoxybenzaldehyde.

To a solution of hexamethylenetetramine (300 g; 2.14 mole) in ethanol (900 ml) and water (600 ml) a mixture of α-bromo-4-trifluoromethoxytoluene and α,α-dibromo-4-trifluoromethoxytoluene (300 g; 1.11 mole; 76:24 mixture) is added. The reaction mixture is stirred and heated at reflux for 3 hours under a nitrogen atmosphere, and then stirred overnight at room temperature.

From the above reaction mixture a cloudy liquid (144.5 g) is isolated and then distilled under vacuum to afford 122.2 g (58%) of title product, a colorless liquid, b.p. 66°–74° C. at 5–7 mm. NMR (in CCl$_4$) [δ=6.15 and 6.75 (AB doublets, 4H, J=8 Hz, aromatics) 8.85 (S, 1H, —CHO)]. IR 1710 cm$^{-1}$ (carbonyl stretch).

The required mixture of α-bromo- and α,α-dibromo-4-trifluoromethoxytoluene is obtained through the bromination of p-trifluoromethoxytoluene by the method of Example 8.

EXAMPLE 2

Preparation of 1,5-Bis[p-(trifluoromethoxy)phenyl]-1,4-pentadien-3-one

Acetone (8.7 g; 0.15 mole) is added to a solution of p-trifluoromethoxybenzaldehyde (57.0 g; 0.30 mole) in methanol (200 ml). The solution is cooled to 20° C. and 10% aqueous sodium hydroxide (8 ml) is added dropwise in about 5 minutes. The reaction mixture is then stirred at room temperature for 1.5 to 2 hours. During this period a yellow solid precipitates from the solution. The mixture is chilled overnight, filtered and the isolated yellow solid dried to afford 24.8 g (41%) of title product, m.p. 121°–123° C. NMR (acetone-d6) [δ=7.0–8.0 (M, 12H, aromatics and vinyl)]; IR 1590–1650 cm$^{-1}$ (several bands).

EXAMPLE 3

Preparation of 1,5-Bis[p-(trifluoromethoxy)phenyl]-1,4-pentadien-3-one-(1,4,5,6-tetrahydro-5,5-dimethyl-2-pyrimidinyl)-hydrazone A mixture of 1,5-bis[p-trifluoromethoxy)phenyl]-1,4-pentadien-4-one (4.02 g; 0.01 mole), (1,4,5,6-tetrahydro-5,5-dimethyl-2-pyrimidinyl)hydrazine hydroiodide (2.70 g; 0.01 mole) and ethanol (25 ml) is stirred and heated at reflux for 3 hours. The ethanol is then stripped from the reaction mixture and the residue washed thoroughly with ether. The residue is then stirred with ether (100 ml) and saturated sodium carbonate solution (50 ml). After about 15 minutes the ether layer is separated, dried and evaporated. The residual yellow solid is recrystallized from a benzene-hexane mixture to afford 2.6 g (50%) of title product, a yellow solid, m.p. 170°–172° C.

Analysis calculated for C$_{25}$H$_{24}$O$_2$N$_4$F$_6$: C 57.05; H 4.56; N 10.65; Found: C 56.42; H 4.59; N 10.46.

EXAMPLE 4

Preparation of 1,5-Bis[p-(trifluoromethoxy)phenyl]-1,4-pentadien-3-one-4,5,6,7-tetrahydro-1H-1,3-diazepin-2-ylhydrazone A mixture of 1,5-bis[p-(trifluoromethoxy)phenyl]-1,4-pentadien-3-one (4.0 g; 0.01 mole), 4,5,6,7-tetrahydro-1H-1,3-diazepine-2-ylhydrazine hydroiodide (2.6 g; 0.01 mole) and isopropyl alcohol (25 ml) is heated at reflux for 2 to 3 hours. The reaction mixture is then cooled to −15° C., and the precipitated material is isolated by filtration and washed with ether. The isolated material is mixed with ether and saturated sodium carbonate solution and the mixture stirred for about 15 minutes. The ether layer is then separated, dried, and concentrated to afford 3.8 g (75%) of title product, a bright yellow solid, m.p. 184.5°–185.5° C.

Analysis calculated for: C$_{24}$H$_{22}$O$_2$N$_4$F$_6$:
C 56.27; H 4.29; N 10.94;
Found: C 56.24; H 4.28; N 10.92.

EXAMPLE 5

Preparation of 1,5-Bis[p-(1,1,2,2-tetrafluoroethoxy)phenyl]-1,4-pentadien-3-one

Aqueous sodium hydroxide (28.1 ml; 10%) is added dropwise, rapidly, to a stirred mixture of p-(1,1,2,2-tetrafluoroethoxy)benzaldehyde (11 ml; 0.069 mole), acetone (2.4 ml; 0.33 mole), absolute alcohol (135 ml) and water (14 ml). The reaction mixture exotherms to 30° C. The reaction mixture is then cooled, the precipitated material is filtered, washed and dried to afford 3.8 g (25%) of title product.

EXAMPLE 6

Preparation of 1,5-Bis[p-(1,1,2,2-tetrafluoroethoxy)phenyl]-1,4-pentadien-3-one-(1,4,5,6-tetrahydro-5,5-dimethyl-2-pyrimidinyl)hydrazone, -hydriodide.

A mixture of 1,5-bis[p-(1,1,2,2-tetrafluoroethoxy)-phenyl]-1,4-pentadien-4-one (6.3 g; 0.135 mole), (1,4,5,6-tetrahydro-5,5-dimethyl-2-pyrimidinyl)hydrazine (3.65 g; 0.135 mole), hydriodic acid (0.5 ml; 51% aqueous) and absolute ethanol (25 ml) is stirred and refluxed for 3.5 hours. The reaction mixture is then cooled, the resulting precipitate filtered and dried to afford 7.1 g (73%) of title product, a bright yellow solid, m.p. 214.5°–216.5° C.

Analysis calculated for C$_{27}$H$_{27}$O$_2$N$_4$F$_8$I: C 45.13; H 3.79; N 7.8;
Found: C 45.37; H 4.05; N .778.

EXAMPLE 7

Preparation of p-Difluoromethylthiotoluene

A mixture of sodium hydroxide (202 g; 4.91 mole), dioxane (300 ml), water (400 ml) and p-thiocresol (70.0 g; 0.55 mole) is stirred, heated to 55° C. and chlorodifluoromethane (94 g; 1.1 mole) is bubbled through the reaction mixture at a rate to maintain the temperature at 55° C. by the reaction exotherm. Addition time is 4 hours. The reaction mixture is then cooled to room temperature, diluted with water (500 ml) and extracted three times with ether. The combined ether extracts are washed with 5% potassium hydroxide solution, water and then dried over sodium sulfate. The ethereal solution is concentrated to afford 134 g of clear yellow liquid. Distillation of same affords 78 g (81%) of title product, a water white liquid, bp. 87°–89° C. at 16–18 m.

EXAMPLE 8

Preparation of α-Bromo-p-difluoromethylthiotoluene

A solution of bromine (18.6 ml; 0.3618 mole) in carbon tetrachloride (25 ml) is added dropwise over two hours to a gently refluxing (~ 55° C.) solution of p-difluoromethylthiotoluene (35.0 g; 0.201 mole) in carbon tetrachloride (120 ml) containing azobisisobutyronitrile (0.1 g) while being irradiated with UV light. The reaction mixture is then stirred for one additional hour at reflux and is then concentrated to afford 62.8 g of a mixture consisting of 73% by weight of α, α-dibromo-p-difluoromethylthiotoluene and 27% by weight of α-bromo-p-difluoromethylthiotoluene (as determined by proton magnetic resonance).

EXAMPLE 9

Preparation of p-Difluoromethylthiobenzaldehyde

To a solution of hexamethylenetetramine (31.2 g; 0.22 mole) in ethanol (90 ml) and water (60 ml) under a nitrogen atmosphere a mixture of α-bromo-p-difluoromethylthiotoluene and α,α-dibromo-p-difluoromethylthiotoluene (31.3 g; 27:73 mixture of Example 8) is added. The reaction mixture is heated at reflux for 2 hours then stirred at room temperature for 16 hours. It is then diluted with water (500 ml) and extracted 3X with ether. The ether layer is washed with water, saturated salt solution and dried over magnesium sulfate. The ethereal solution is concentrated to afford 15.0 g (80%) of the title product, a yellow oil; 90% real by NMR.

EXAMPLE 10

Preparation of
1,5-Bis-{p-[(difluoromethyl)thio]phenyl}-1,4-pentadien-3-one

Acetone (1.1 ml; 0.051 mole) and p-difluoromethylthiobenzaldehyde (6.0 g; 0.032 mole) are dissolved in a mixture of ethanol (53 ml) and water (5.3 ml). The solution is stirred, cooled below 25° C., and a solution of sodium hydroxide (10 ml of 10%) added dropwise. After the addition is completed, the reaction mixture is cooled to 15° C., the precipitated solids are filtered, washed and dried to afford 3.5 g of title product. The product can be recrystallized from methanol.

EXAMPLE 11

1,5-Bis{p-[(difluoromethyl)thio]phenyl}-1,4-pentadien-3-one
1,4,5,6-tetrahydro-5,5-dimethyl-2-pyrimidinyl)hydrazone A mixture of 1,5-bis{p-[(difluoromethyl)thio]phenyl}-1,4-pentadien-3-one (1.3 g; 0.0033 mole), (1,4,5,6-tetrahydro-5,5-dimethyl-2-pyrimidinyl)hydrazine hydroiodide (0.88 g; 0.0033 mole), hydriodic acid (0.2 ml; of 51% aqueous) and ethanol (10 ml) is stirred and heated at reflux for 18 hours, and then chilled in an ice bath for one hour. The precipitated solid (2.0 g) is filtered and stirred with a mixture of ethyl acetate (10 ml) and saturated sodium carbonate solution for 0.5 hour. The ethyl acetate layer is then separated, dried over magnesium sulfate and stripped under high vacuum to afford 0.85 g of title product, an orange solid, m.p. 155°–156° C.

Analysis calculated for $C_{25}H_{25}N_4F_4S_2$:
C 57.45; H 5.02; N 10.72;
Found: C 56.75; H 5.15; N 10.42.

EXAMPLE 12

Preparation of p-Difluoromethoxybenzaldehyde

Sodium hydroxide (48 g; 1.2 mole) is added to a stirred suspension of p-hydroxybenzaldehyde (48.9 g; 0.4 mole) in dioxane (142 ml) and water (87 ml). The mixture is heated to 70° C. and chlorodifluoromethane (33 g) added slowly. When this addition is completed, 50% sodium hydroxide solution (32 ml) is added to the reaction mixture, followed by the slow addition of chlorodifluoromethane (33 g). This recharging is repeated three times, and a total of 96 g (2.4 mole) of sodium hydroxide and 133 g (1.54 mole) of (1.54 mole) of chlorodifluoromethane is used in the reaction. The reaction mixture is cooled down, diluted with water (1500 ml) and extracted with ether several times. The ether layers are combined, washed with 10% sodium hydroxide and then dried over magnesium sulfate. Concentration of the ethereal solution yields 39 g (57%) of a yellow oil. This oil is purified by chromatography on a silica gel column using a mixture of hexane:methylene chloride (1:3), to afford 27 g (39%) of title product.

EXAMPLE 13

Preparation of
1,5-Bis[p-(difluoromethoxy)phenyl]-1,4-pentadien-3-one

A mixture of p-difluoromethoxybenzaldehyde (10.7 g; 0.0622 mole), acetone (2.2 ml; 0.0296 mole, ethanol (103 ml) and water (10 ml) is added dropwise, rapidly, and with stirring to an aqueous sodium hydroxide solution (25.5 ml; 10%). The reaction mixture exotherms to 30° C. and a precipitate forms. The precipitate is filtered, washed and dried to afford 9.0 g (97.2%) of title product.

EXAMPLE 14

Preparation of
1,5-Bis[p-(difluoromethoxy)phenyl]-1,4-pentadien-3-one-(1,4,5,6-tetrahydro-5,5-dimethyl-2-pyrimidinyl)-hydrazone.

A mixture of 1,5-bis[p-difluoromethoxy)phenyl]-1,4-pentadien-3-one (4.5 g/ 0.0123 mole), 1,4,5,6-tetrahydro-5,5-dimethyl-2-pyrimidinylhydrazine (3.3 g; 0.123 mole), hydriodic acid (0.5 ml; 51% aqueous) and absolute ethanol (25 ml) is heated at reflux for 3 hours. The reaction mixture is then cooled down, the precipitate isolated by filtration to afford 5.5 g (72%) hydriodide salt of the title product, m.p. 164°–166° C.

Analysis calculated for $C_{25}H_{29}O_2N_4F_4I$:
C 48.55; H 4.40; N 9.06;
Found: C 47.70; H 4.36; N 9.06.

The above salt (6.9 g) is mixed with ethyl acetate (20 ml) and saturated sodium carbonate solution (20 ml), and the mixture stirred for one hour. The organic phase is then separated, washed with water, dried over magnesium sulfate and concentrated to yield 5.4 g (99%) of an orange solid. Recrystallization from isopropanol affords 4.0 g (73%) of title product, m.p. 152°–154° C.

Analysis calculated for $C_{25}H_{26}O_2N_4F_4$: C 61.21; H 5.34; N 11.42; Found: C 61.01; H 5.54; N 11.37.

EXAMPLE 15

Preparation of
1,5-Bis[p-(trifluoromethoxy)phenyl]-1,4-pentadien-3-one-(1,4,5,6-tetrahydro-2-pyrimidinyl)hydrazone.

By the procedure of Example 14, except substituting 1,4,5,6-tetrahydro-2-pyrimidinylhydrazine hydroiodide for 1,4,5,6-tetrahydro-5,5-dimethyl-2-pyrimidinylhydrazine hydroiodide, the title compound, a yellow solid, is obtained, m.p. 140°–142° C.

EXAMPLE 16

Preparation of
1,5-Bis[p-(difluoromethoxy)phenyl]-1,4-pentadien-3-one N,N'-diethylamidinohydrazone By following the procedure of Example 14, but replacing 1,4,5,6-tetrahydro-5,5-dimethyl-2-pyrimidinylhydrazine hydroiodide with N,N'-diethylamidinohydrazine hydroiodide affords the title compound, a yellow solid, m.p. 97°–99° C.

EXAMPLE 17

Preparation of
1,5-Bis[p-chloro-m-(difluoromethoxy)phenyl]-1,4-pentadien-3-one-(1,4,5,6-tetrahydro-2-pyrimidinyl)hydrazone By the procedures of Examples 7 through 10, and starting with 2-chloro-5-methylphenol, 1,5-bis[p-chloro-m-difluoromethoxy)phenyl]-1,4-pentadien-3-one is prepared. This pentadienone is then reacted with 1,4,5,6-tetrahydro-2-pyrimidinylhydrazine hydroiodide by the procedure of Example 11 to afford the title compound, a yellow solid, m.p. 177°–180° C.

EXAMPLE 18

Preparation of
1,5-Bis[p-(2,2-dichloro-1,1-difluoroethoxy)phenyl]-1,4-pentadien-3-one-(1,4,5,6-tetrahydro-5,5-dimethyl-2-pyrimidinyl)hydrazone p-Cresol is condensed with 1,1-dichloro-2,2-difluoroethylene to yield p-2,2-dichloro-1,1-difluoroethoxytoluene.

The procedures of Examples 8 through 10 are utilized to convert the above compound into 1,5-bis[p-(2,2-dichloro-1, 1-difluoroethoxy)phenyl]-1,4-pentadien-3-one.

Reaction of this pentadienone with 1,4,5,6-tetrahydro-5,5-dimethyl-2-pyrimidinylhydrazine hydroiodide by the procedure of Example 11 affords the title product, a yellow solid, m.p. 177°–180° C.

Analysis calculated for $C_{27}H_{26}Cl_4F_4N_4O_2$: C 49.41; H 3.99; N 8.54; Found: C 48.22; H 3.96; N 8.08.

EXAMPLE 19

Preparation of
1,5-Bis[p-(difluoromethoxy)phenyl]-1,4-pentadien-3-one (4-methyl-2-imidazolin-2-yl)hydrazone.

By the procedure of Example 14, but substituting 4-methyl-2-imidazolin-2-ylhydrazine dihydrochloride for 1,4,5,6-tetrahydro-5,5-dimethyl-2-pyrimidinylhydrazine hydroiodide, the title compound, a bright yellow solid, is obtained.

EXAMPLE 20

Preparation of
1,5-Bis[p-(trifluoromethylthio)phenyl]-1,4-pentadine-3-one-(1,4,5,6-tetrahydro-5,5-dimethyl-2-pyrimidinyl)-hydrazone By the procedures of Examples 7 through 10, the compound: 1,5-bis[p-(trifluoromethylthio)phenyl]-1,4-pentadine-3-one is prepared from p-trifluoromethylthiotoluene.

Reaction of this pentadienone with 1,4,5,6-tetrahydro-5,5-dimethyl-2-pyrimidinylhydrazine by the procedure of Example 11 yields the title product, a yellow solid, m.p. 172° C.–174° C.

EXAMPLE 21

Preparation of
1,5-Bis[m-bromo-p-(difluoromethoxy)phenyl]1,4-pentadien-3-one-(1,4,5,6-tetrahydro-5,5-dimethyl-2-pyrimidinyl)hydrazone By the procedures of Examples 7 through 10, the compound: 1,5-bis[m-bromo-p-(difluoromethoxy)-phenyl]-1,4-pentadien-3-one is prepared from 2-bromo-4-methylphenol.

Reaction of this pentadienone with 1,4,5,6-tetrahydro-5,5-dimethyl-2-pyrimidinylhydrazine hydroiodide by the procedure of Example 11, affords the title product, a dark yellow solid.

EXAMPLE 22

Evaluation of the Insecticidal Activity of the Compounds of the Invention

The activity of the hereinabove compounds of this invention is demonstrated by the following tests, wherein pentadienone hydrazones are evaluated against test insect species at rates ranging from 10 to 1000 ppm. Test formulations and procedures used for evaluation are as follows:

Test Formulations

A. 100 Mg of the test material is weighed, placed in a funnel over a 113 g narrow-mouth bottle, and rinsed into the bottle with a 35 ml scoop of acetone, followed by a scoop of water and another scoop of acetone to yield 1000 ppm in 65% acetone. If the material is not soluble, it is broken up with a glass rod and used as a suspension.

B. This stock solution ("A") is used to make 300 ppm solutions or suspensions by pipetting 30 ml of "A" into a bottle containing 70 ml of 50% acetone to yield 300 ppm. Further dilutions in 50% acetone are made as required.

C. Tests requiring 10 ppm in acetone solutions: 1 ml of "A" is pipetted into 99 ml of acetone to yield 10 ppm. Additional dilutions are made using 50% acetone as required.

Initial Tests

Tobacco Budworm—*Heliothis virescens* (Fabricius)

A cotton plant with 2 true leaves expanded is dipped for 3 seconds with agitation in 300 ppm solution. A 1.27 to 1.91 cm square of cheesecloth with about 50 to 100 budworm eggs 0–24 hours old is also dipped in the test solution and placed on a leaf of the cottom plant, all being placed in the hood to dry. The leaf with the treated budworm eggs is removed from the plant and placed in a 236.6 ml (8-oz) Dixie cup with a wet 5 cm piece of dental wick and covered with a lid. The other leaf is placed in a similar cup with a wick and a piece of cheesecloth infested with 50–100 newly hatched larvae is added before covering the cup with a lid. After 3 days at 26.7° C., 50% r.h., observations of egg hatch are made, as well as kill of newly hatched larvae, any inhibition of feeding, or interference of any sort with normal development.

Southern Armyworm—*Spodoptera eridania* (Cramer)

A Sieva lima bean plant with just the primary leaves expanded to 1.91 cm is dipped for 3 seconds with agitation in the "A" solution of 1000 ppm and set in the hood to dry. Following this, one leaf is placed in a 9 cm petri dish which contains a moist filter paper in the bottom and 10 third-instar armyworm larvae about 1 cm long. This dish is covered and held at 26.7° C., and 50% r.h. After 2 days, mortality counts and estimates of the amount of feeding are made. Compounds showing partial kill and/or inhibition of feeding are held for an extra day for further observations. Those materials which produce greater than 75% mortality, or which show only trace feeding damage are further tested.

All compounds showing activity as defined above are retested, using the second leaf on the bean plant, after an interval of 7 days from original treatment, as an assay of residual activity.

Secondary Tests

Tobacco Budworm—*Heliothis virescens* (Fabricius)—Third Instar

Three cotton plants with just expanded cotyledons are dipped in 1000 ppm solution and placed in the hood to dry. When dry, each cotyledon is cut in half, and each half is placed in one of ten 29.6 ml plastic medicine cups containing a 1.25 cm dental wick saturated with water and one third-instar budworm larva is added. The cup is capped and held for 3 days at 26.7° C., 50% r.h., after which mortality counts are made. Compounds killing more than 75% of the larbae are further tested.

Cabbage Looper—*Trichoplusia ni* (Hübner)—Third Instar

A true leaf of a cotton plant is dipped into the test solution, agitated for 3 seconds, and removed to dry in an exhaust hood. When dry, the leaf is placed in a 9.0 cm petri dish with moist filter paper on the bottom. Ten third-instar larvae are added and the lid placed on the dish. Mortality counts are made after 3 days at 26.7° C., and 50±10% r.h. Compounds killing more than 75% of the loopers are further tested.

Imported Fire Ant Bait Toxicant Tests (*Solenopsis invicta* Buren) Test Procedure Tests are conducted in 30 ml disposable plastic medicine cups (40 mm ID at the top, tapering to 32 mm ID at the bottom, 38 mm high). A hole (6 mm diam.) is drilled through the bottom of each cup and a layer of plaster of Paris and builders' cement (9:1 ratio) poured over the bottom. The plaster mixture covers the hole and acts as a wick to draw up water when the cup is placed on a 8 mm thick foam rubber pad saturated with water. The cups are placed in a tray and covered by another tray inverted to prevent rapid evaporation of water from the foam pad. Moisture is necessary to keep the humidity in the cups high and thereby prevent desiccation of the ants. The cement is added to make a hard mixture through which the ants cannot tunnel and escape.

Twenty worker ants from field-collected colonies are placed in each test chamber ca. 24 hr preceding the start of the test. This pretreatment holding period allows time for recovery of the ants from handling and for orientation to the containers.

Candidate chemicals are dissolved directly in the food material; e.g., soybean oil. The toxic solution is offered to the ants on cotton swabs saturated with the material and placed in the test chamber in small vial caps. Preliminary tests are conducted at concentrations of 1.0, 0.1, and 0.01 percent.

The ants are allowed to feed as desired on the toxic bait for 24 hr. After this exposure period, the toxicant is removed from the chamber and the ants remain without food for an additional 24 hr. At the end of this time new vial caps containing cottom swabs saturated with soybean oil are placed in the chamber and ldft for the remainder of the test period. Knockdown and mortality counts are made at intervals of 1, 2, 3, 6, 8, 10, and 14 days following initial exposure. Each test consists of 3 replications. Room temperature is maintained at 23.9±1° C.

Data obtained are reported in Table I below.

TABLE I
EVALUATION OF PENTADIENONE HYDRAZONES AS INSECTICIDES. Percent Mortality.

| Compound | Eggs 300 ppm | tobacco budworm Larvae 300 ppm | Larvae 100 ppm | Larvae 10 ppm | Southern Armyworms 1000 ppm | 100 ppm | 10 ppm | 7 days | Third-Instar Tobacco Budworms 1000 ppm | 100 ppm | Cabbage Looper 1000 ppm | 100 ppm |
|---|---|---|---|---|---|---|---|---|---|---|---|---|
| (F$_3$CO)–C$_6$H$_4$–CH=CH)$_2$–C=N–NH– (piperidine ring) | 0 | 90 | 0 | 0 | 100 | 100 | 50 | | 100 | 0(R) | 100 | 90 |
| (F$_3$CO)–C$_6$H$_4$–CH–CH$_2$)$_2$–C=N–NH–N(C(CH$_3$)$_2$CH$_2$)$_2$NH | 0 | 100 | 0 | 0 | 100 | 100 | 0 | | 100 | 100 | 100 | 100 |
| (F$_2$CH–CF$_2$O)–C$_6$H$_4$–CH=CH)$_2$–C=N–NH–N(C(CH$_3$)$_2$CH$_2$)$_2$NH · HI | 0 | 100 | 100 | 0 | 100 | 100 | 0 | | 100 | 100 | 100 | 100 |
| (F$_2$CHO)–C$_6$H$_4$–CH–CH$_2$)$_2$–C=N–NH–N(C(CH$_3$)$_2$CH$_2$)$_2$NH | 0 | 90 | 80 | 0 | 100 | 90 | 0 | | R | 30 | 100 | 50 |
| (F$_2$CH–S)–C$_6$H$_4$–CH–CH$_2$)$_2$–C=N–NH–N(C(CH$_3$)$_2$CH$_2$)$_2$NH · HI | 0 | 90 | 50 | 0 | 100 | 100 | 0 | | 100 | 100 | 90 | 50 |
| (F$_2$CHO)–C$_6$H$_4$–CH=CH)$_2$–C=N–NH–N(C(CH$_3$)$_2$CH$_2$)$_2$NH | 0 | 90 | 50 | 0 | 100 | 100 | 0 | 100* | 0(R) | R | 100 | 100 |
| (F$_2$CHO)–C$_6$H$_4$–CH=CH)$_2$–C=N–NH– (piperidine ring) | 0 | 0 | 0 | (R) | | | | | | | | |

TABLE I -continued

| Structure | | | | |
|---|---|---|---|---|
| (F₂CHO—⟨phenyl⟩—CH=CH—)₂ C=N—NH—C(=N—C₂H₅)—NHC₂H₅ | 0 | 0 | 0 | 90 |
| (Cl₂CH—CF₂O—⟨phenyl⟩—CH=CH—)₂ C=N—NH—[4,4-dimethyl-oxazinyl] | 0 | 0 | 0 | 0 |
| {⟨cyclohexyl with Cl, F₂CHO⟩—CH=CH—CH— C=N—NH—[tetrahydropyrimidinyl]}₂ | 0 | 0 | 0 | 50 |
| (F₂CHO—CH—CH₂)₂ C=N—NH—[5-methyl-pyrrolidinyl] | 0 | 0 | 0 | 100 |

R - Reduced feeding;
* = at 1000 ppm.

Evaluation of Pentadiene Hydrazones as Insecticides. Percent Mortality at 14 days

| Compound | Imported Fire Ant | |
|---|---|---|
| | 10,000 ppm | 1000 ppm |
| (F₃CO—⟨phenyl⟩—CH=CH—)₂ C=N—NH—[piperidinyl] | 95 | 87 |
| (F₃CO—⟨phenyl⟩—CH=CH—)₂ C=N—NH—[4,4-dimethyl-tetrahydropyrimidinyl] | 100 | 97 |
| (F₂CH—CF₂O—⟨phenyl⟩—CH=CH—)₂ C=N—NH—[5,5-dimethyl-tetrahydropyrimidinyl] · HI | 100 | 36 |

TABLE I -continued

| Structure | | |
|---|---|---|
| (F₂CHO)—⟨phenyl⟩—(CH=CH—)₂—C(=N—NH—)N(H)—CH₂—C(CH₃)₂—CH₂—N(H) · HI | 100 | 25 |
| (F₂CH—S)—⟨phenyl⟩—(CH=CH—)₂—C(=N—NH—)N(H)—CH₂—C(CH₃)₂—CH₂—N(H) | 100 | 95 |

We claim:

1. The compound 1,5-bis-[p-(trifluoromethoxy)-phenyl]-1,4-pentadien-3-one (1,4,5,6-tetrahydro-5,5-dimethyl-2-pyrimidinyl)hydrazone, or inorganic acid addition salts thereof.

2. A method for controlling insects comprising: contacting said insects, their habitat, and/or their food supply, with an insecticidally effective amount of a compound and having the structure:

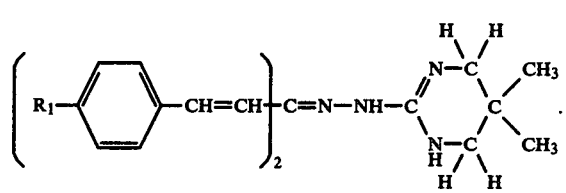

wherein $R_1$ is trifluoromethoxy.

3. The method according to claim 2, wherein the insects are ants, Family Formicidae; and the compound is applied at the rate of from 2.5 g/hectare to 37.5 g/hectare.

4. The method according to claim 2, wherein the insects are termites, cockroaches, grasshoppers, flies and ants, Family Formicidae, and the compound is applied incorporated in a bait at a concentration of from 0.125% to 2.0% by weight.

5. The method according to claim 2 wherein the ants are the southern fire ant *Solenopsis xyloni*, the black imported fire ant *Solenopsis richteri* and the red imported fire ant *Solenopsis invicta*.

6. A method for protecting agronomic crops, trees, shrubs and ornamentals, from attack by insects comprising: applying to said crops an insecticidally effective amount of a compound and represented by the formula:

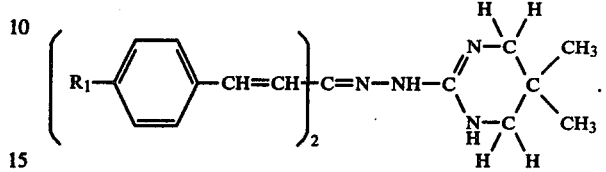

wherein $R_1$ is trifluoromethoxy.

7. The method according to claim 6, wherein said insects are ants, Family Formicidae; and said compound is applied at the rate of from 2.5 g/hectare to 37.5 g/hectare.

8. The method according to claim 6, wherein the insects are termites, cockroaches, grasshoppers, flies or ants, Family Formicidae, and the compound is applied incorporated in a bait at a concentration of from 0.125% to 2.0% by weight.

9. The method according to claim 6, wherein the ants are the southern fire ant *Solenopsis xyloni*, the black imported fire ant *Solenopsis richteri* or the red imported fire ant *Solenopsis invicta*.

* * * * *